United States Patent
Meron

(10) Patent No.: US 10,288,593 B2
(45) Date of Patent: May 14, 2019

(54) DEVICE FOR MEASURING WATER POTENTIAL IN PLANT TISSUE

(71) Applicant: SATURAS LTD, Efrat (IL)

(72) Inventor: Moshe Meron, Upper Galillee (IL)

(73) Assignee: Saturas Ltd., Efrat (IL)

( * ) Notice: Subject to any disclaimer, the term of this patent is extended or adjusted under 35 U.S.C. 154(b) by 145 days.

(21) Appl. No.: 15/107,893

(22) PCT Filed: Dec. 23, 2014

(86) PCT No.: PCT/IL2014/051120
§ 371 (c)(1),
(2) Date: Jun. 23, 2016

(87) PCT Pub. No.: WO2015/097699
PCT Pub. Date: Jul. 2, 2015

(65) Prior Publication Data
US 2016/0327536 A1    Nov. 10, 2016

Related U.S. Application Data

(60) Provisional application No. 61/919,859, filed on Dec. 23, 2013.

(51) Int. Cl.
*G01N 7/10* (2006.01)
*G01N 33/00* (2006.01)
(Continued)

(52) U.S. Cl.
CPC ....... *G01N 33/0098* (2013.01); *A01G 25/167* (2013.01); *G01N 7/10* (2013.01);
(Continued)

(58) Field of Classification Search
CPC .......... G01N 13/04; G01N 13/02; G01N 7/10; G01N 33/0098; G01N 2333/415
See application file for complete search history.

(56) References Cited

U.S. PATENT DOCUMENTS

| | | | |
|---|---|---|---|
| 4,455,864 A | 6/1984 | Wallner | |
| 4,755,942 A * | 7/1988 | Gardner | A01G 25/16 |
| | | | 47/1.01 R |

(Continued)

FOREIGN PATENT DOCUMENTS

| | | |
|---|---|---|
| CN | 102905515 | 1/2013 |
| EP | 0060447 | 9/1982 |

(Continued)

OTHER PUBLICATIONS

International Search Report and Written Opinion issued in application No. PCT/IL2014/051120 dated Apr. 20, 2015.

(Continued)

*Primary Examiner* — Justin N Olamit
(74) *Attorney, Agent, or Firm* — Knobbe, Martens, Olsen & Bear, LLP

(57) ABSTRACT

A device and a system are for measuring fluid potential in a plant tissue by measuring pressure changes caused due to osmosis of the plant fluid. The measuring device includes a compartment having a ridged body configured for containing an osmoticum. The compartment has at least one opening; at least two selective barrier layers, such as a membrane positioned at least over the openings of the compartment; and at least one pressure sensor configured for detecting changes in pressure of fluid in the compartment. The selective barrier is located for selectively allowing water transfer between the plant fluid and the osmoticum in the compartment. The compartment is configured such that there is a direct contact between the plant fluid and the osmoticum therein via the selective barrier.

13 Claims, 12 Drawing Sheets

(51) Int. Cl.
  *G01N 13/04* (2006.01)
  *A01G 25/16* (2006.01)
  *G01N 33/483* (2006.01)
  *B01D 61/00* (2006.01)

(52) U.S. Cl.
  CPC ......... *G01N 13/04* (2013.01); *G01N 33/4833* (2013.01); *B01D 61/005* (2013.01); *G01N 2333/415* (2013.01)

(56) References Cited

U.S. PATENT DOCUMENTS

| | | | |
|---|---|---|---|
| 9,144,640 B2 * | 9/2015 | Pudil | A61M 1/1696 |
| 9,408,251 B2 * | 8/2016 | Grady | H04W 84/18 |
| 9,766,173 B2 * | 9/2017 | Stroock | G01N 13/02 |
| 2012/0079876 A1 * | 4/2012 | Stroock | G01N 13/02 |
| | | | 73/64.51 |
| 2014/0109658 A1 * | 4/2014 | Kah, Jr. | G01N 5/02 |
| | | | 73/73 |

FOREIGN PATENT DOCUMENTS

| | | |
|---|---|---|
| JP | 2005328715 A | 12/2015 |
| WO | WO 98/04915 A1 | 2/1998 |
| WO | WO 2004/083829 | 9/2004 |
| WO | WO 2015/097699 A1 | 7/2015 |

OTHER PUBLICATIONS

Fullerton et al; "Method to improve the accuracy of membrane osmometry measures of protein molecular weight" Journal of Biochemical and Biophysical Methods vol. 26, Issue 4, , pp. 299-307.(1993).

Luttge et al; "Day-Night Variations in Malate Concentration, Osmotic Pressure, and Hydrostatic Pressure in Cereus validus" Plant Physiol. 75, pp. 804-807. (1984).

\* cited by examiner

DEVICE FOR MEASURING WATER POTENTIAL IN PLANT TISSUE

CROSS-REFERENCE TO RELATED PATENT APPLICATIONS

This application is the U.S. National Phase under 35 U.S.C. § 371 of International Application No. PCT/IL2014/051120, filed Dec. 23, 2014, designating the U.S., and published in English as WO 2015/097699 A1 on Jul. 2, 2015, which claims priority to U.S. provisional patent application No. 61/919,859 filed on Dec. 23, 2013, which is incorporated herein by reference in its entirety.

FIELD OF THE INVENTION

The present invention generally relates to devices, apparatuses, detectors, systems and methods for measuring water potentials in plants and more particularly to devices, apparatuses, osmometers, systems and methods for measuring water potential in plants via osmometry.

BACKGROUND OF THE INVENTION

Water potential in plants is key measurement for determining the water activity in a living cell. Measured water potential in plants is expressed in pressure units, with negative magnitudes. Water potential in plants ranges from $\sim$−0.3 MPa at the roots, through $\sim$−1 MPa (Mega-Pascal) in the stem and $\sim$−2 MPa at the canopy and towards $\sim$−100 MPa in the atmosphere. As water flow from high potential to low potential, so does water in plants flow from the soil to roots via the stem and the canopy to the atmosphere. Accurate measurement of within plant water potential is essential information for determination of irrigation state of the crop.

Continuous monitoring of water potential in crops is key factor for determination of the optimal irrigation in precision agriculture. The invention described here uses osmometer based sensor to accurately follow the crop water potential.

While connecting measuring devices into xylem vessels disrupts the soil-plant-atmosphere water continuum, the feasibility of measuring apoplastic (inter cellular tissue space) water potentials of abraded stem tissue by psychrometry was demonstrated by McBurney and Costigan (1984), and the instrument was developed by Dixon and Tyree (1984). That approach is commercialized now by ICT International of Australia (Anon. 2013). The rigorous operational requirements of this instrument limit its use to scientific applications, but the device not suitable to practical farming. A novel MEMS device for water potential measurement, was patented by Cornell University under provisional US application Ser. No. 61/170,223, April 2009, PCT publication WO2010/121176 A2 October 2010, entitled "Microfluidic Xylem Probe" and U.S. Pat. No. 8,695,407. This probe is inserted into the stem and measures the water potential via the vapor phase, which is in essence another implementation of a psychrometer. Membrane osmometry is a well-known method, used for many decades in various technical forms (e.g. U.S. Pat. No. 4,455,864 of 1984, UK patent GB32261513 of 1992). It consists of two chambers separated with a semi-permeable membrane: The sealed compartment is filled with known osmotic potential solution, and connected to a pressure sensor; the other chamber contains the fluid with unknown osmotic potential due to molecular weight and/or solute concentration. Since only water molecules can pass through the membrane, water is flowing from high water potential to low. The unknown solution's potential is calculated from the pressure change in the sealed compartment. The invention will use the osmometer principle to measure the stem water potential in the fluid phase by tight contact of the sensor membrane with the stem sap.

U.S. Pat. No. 4,455,864 discloses a membrane osmometer for direct measurement of osmotic pressures. The osmometer includes a pressure measuring chamber for receiving pure solvent, a sample chamber separated therefrom for receiving solution to be tested, and a semi-permeable membrane contacting a support plate coarsely pervious to liquids, the membrane being located on the side of the support plate adjacent to the sample chamber, wherein the sample chamber comprises, on its surface nearest the membrane, a conical annular surface which, when the sample chamber and pressure measuring chamber are assembled, presses an elastic sealing ring against both the surface of the membrane facing the sample chamber and against an inner surface of the pressure measuring chamber Patent application No. EP0060447 discloses a sample chamber for receiving a sample liquid to be investigated in a membrane osmometer having a sample chamber open to the atmosphere, characterized in that one or more bores or channels are provided in the walls of the chamber, leading from outside into the interior of the sample chamber and opening out in the vicinity of the outer edge of the free portion of the semipermeable membrane.

Patent application No. WO 2004/083829 discloses a membrane osmometer that comprises a semipermeable membrane whose one side is in contact with a solution to be measured that is located in the measuring cell and whose other side is in contact with a solution to be analyzed. A measuring device measures a pressure difference in the measuring cell or a volumetric flow through the membrane. The solution to be measured contains ligands with binding sites and receptors with opposing binding sites whereby enabling the ligands and receptors to form ligand complexes by a binding of the binding sites to the opposing binding sites. The solution to be analyzed contains analytes with a binding site for binding to the opposing binding sites of the receptors. The semipermeable membrane is permeable to analytes and is impermeable to receptors and ligands. During a method for selectively determining a specific analyte in the solution to be analyzed, the analytes diffuse, at least in part, out of the solution to be analyzed and into the measuring cell via the semipermeable membrane. As a result, an equilibrium of ligands, receptors and ligand complexes changes inside the solution to be measured thus effecting a change in pressure inside the measuring cell that can be measured by the measuring device.

Patent application No. WO 2004/083828 discloses a membrane osmometer that is suited for quantitatively determining analytes, which represent low-molecular affinity ligands of a high-molecular affinity receptor, and to a method for quantitatively determining analytes of this type. The inventive method presents an advantageous form of the competitive affinity assay. This method is characterized in that the semipermeable membrane of the inventive membrane osmometer is used as a signal generator and as an interface to the medium phase. Inside the inventive sensory membrane osmometer, the semipermeable membrane is located between a sensory liquid phase and a medium phase. According to the invention, an impermeable affinity receptor and an impermeable competition ligand are located in the sensory liquid phase, and the membrane is permeable to the analytes. According to the invention, the osmotic partial pressure of the impermeable affinity binding partners and or the hydraulic effect of the affinity bonds between the impermeable affinity binding partners and in a network liquid is recorded as a measure of the analyte concentration. To this end, a measuring device is used for measuring the pressure difference over the semipermeable membrane or the volumetric flow through the semipermeable membrane.

SUMMARY OF THE INVENTION

According to one aspect of the present invention, there is provided a device for measuring fluid potential in a plant tissue that comprises: (a) a compartment having a ridged body configured for containing therein an osmoticum, the compartment comprising at least one opening; (b) at least two selective barrier layers positioned at least over the at least one opening of the compartment for selectively allowing fluid transfer between the plant fluid and the osmoticum in the compartment; and (c) at least one pressure sensor configured for detecting changes in pressure of fluid in the compartment, the changes are related to the fluid potential of the plant tissue, wherein the compartment is configured such that there is a direct contact between the plant fluid and the osmoticum therein via the at least two selective barrier layers.

Optionally, the selective barrier is a membrane. The membrane may be one of: a reverse osmosis (RO) membrane, forward osmosis (FO) membrane or a Nano filtration (NF) membrane.

Additionally or alternatively, the selective barrier (whether a membrane or not) covers at least partially inner walls of the compartment such as to cover the at least one opening of the compartment.

According to some embodiments, the osmoticum is a water absorbent hydrogel, which optionally comprises Poly-EthyleneGlycol (PEG).

The device according to any of the embodiments above, wherein the at least one pressure sensor may be: at least one piezoelectric transducer sensor; at least one strain gauge sensor or a combination thereof.

The device according to any one or more of the embodiments above, wherein the compartment optionally has an elongated shape having at least one open edge covered by said selective barrier.

The device according to any of the embodiments above, optionally further comprising a microprocessor and a transmitter connected to the at least one sensor for reading, digitizing, and transmitting sensor data thereby.

The device may optionally further comprise at least one Micro Electro-Mechanical System (MEMS) sensor unit comprising a pressure sensors and a data processor and transmitter, which are embedded therein.

The device according to any of the embodiments above, wherein the transmitter is optionally configured for wirelessly transmitting one of: RF (radio frequency) signals or IR (Infrared) signals.

The device according to any of the embodiments above, wherein the sensor optionally comprises a sensing unit and a microprocessor which controls the measurement and converts analog voltage outputted by the sensing unit into water potential correlated therewith and the water potential into a digital signal indicative thereof, which can then be transmitted via the transmitter.

According to some embodiments, the transmitter is configured for transmitting signals to a local area mesh network, serving as a relay station forwarding the data to a much more remote central unit for further processing and presentation of data.

The device according to any of the embodiments above, wherein the compartment is optionally configured for being hydraulically connected to a vascular conduit of the plant, wherein the fluid potential that is measured is plant sap water conducted through the vascular conduit. The vascular conduit may be for example the xylem of the plant.

The device according to any of the embodiments above, wherein the compartment optionally forms a flattened shape forming a cavity for containing the osmoticum therein and a single opening, wherein the at least two selective barrier layers are located over the opening of the compartment at an internal or external side thereof.

The device according to any of the embodiments above—wherein the fluid potential within the cavity is initially set to be lower than the minimal potentials expected in the plant tissue to be measured According to other aspects of the present invention, there is provided a method for measuring fluid potential in a plant tissue, the method comprising the steps of: (a) placing at least part of a measuring device inside the plant such that it creates hydraulic continuum with the plant tissue, the measuring device comprising a compartment containing therein an osmoticum having at least one opening, at least one pressure sensor and at least two selective barrier layers positioned over the at least one opening of the compartment, the selective barrier is configured to selectively allow transfer of water therethrough, while blocking transfer of other ingredients in the plant fluid; (b) sensing changes in pressure caused due to osmosis based flow of fluids into or out of the compartment caused to equilibrate the chemical potential of the plant tissue fluid and the osmoticum in the compartment; and (c) outputting data indicative of the sensed pressure, the changes are related to the fluid potential of the plant tissue.

Optionally the method further comprises the steps of: (a) receiving outputted data from the sensor; and (b) calculating the fluid potential in the plant according to the sensed pressure at each given timeframe.

The method optionally further comprises transmitting data outputted by the at least one pressure sensor to a processing unit, configured for conducting calculation of the fluid potential associated with the sensor output data.

Additionally or alternatively, the measuring device is placed in proximity to at least one vascular conduit of the plant.

According to some embodiments, the measuring device is inserted to the apoplast of the stem of the plant.

According to yet other aspects of the present invention, there is provided a system for measuring fluid potential in a group of plants, the system comprising: (a) a multiplicity of measuring devices each inserted into a different plant of the plants group in a location in which each device creates hydraulic continuum with the tissue of each of the plants, wherein each device comprises a compartment having at least one opening configured for containing an osmoticum therein, at least one pressure sensor, at least two selective barrier layers positioned over the at least one opening of the compartment; and (b) a central unit configured for receiving sensor data from all measuring devices in real time and calculating fluid potential of each plant of the group based on the sensor data associated therewith.

Optionally, the central unit is further configured for at least one of: (a) calculating at least one condition of each of the plants in the group and/or of the entire group, according to fluid potential of each plant; and (b) presenting the calculated at least one condition of each plant and/or of the entire group.

The at least one condition may comprise, for instance, at least one of: irrigation condition; fertilization condition.

Optionally, the central unit comprises at least one receiver for receiving sensor data. This receiver may be configured for wirelessly receiving signals from the pressure sensors of the multiple devices over a wireless link.

In some embodiments, each sensor of each measuring device of the system comprises a sensing unit and a microprocessor, which controls the measurement and converts analog voltage outputted by the sensing unit into water potential correlated therewith and the water potential into a digital signal indicative thereof, which can then be transmitted via the transmitter. The transmitter is optionally configured for transmitting signals to the central unit via a RF or IR communication based local area mesh network.

According to other aspects of the present invention, there is provided a device for measuring fluid potential in a plant tissue, the device comprising: (a) at least two selective barrier layers encapsulating an osmoticum therein for selectively allowing fluid transfer between the plant fluid and the osmoticum therein; and (b) at least one pressure sensor configured for detecting changes in pressure of fluid in the at least two barrier layers, the changes are related to the fluid potential of the plant tissue.

BRIEF DESCRIPTION OF THE DRAWINGS

FIG. 1A shows an isometric view of the measuring device; FIG. 1B shows a cross-sectional view of the measuring device; and FIG. 1C shows a bottom view of the measuring device.

FIG. 2A shows an exploded view of the device; FIG. 2B shows a perspective side view of the device; and FIG. 2C shows a perspective elevated view of the device.

FIG. 9A shows an isometric view of the measuring device; FIG. 9B shows a cross-sectional view of the measuring device; and FIG. 9C shows a bottom view of the measuring device.

DETAILED DESCRIPTION OF SOME EMBODIMENTS OF THE INVENTION

Figure 1A:
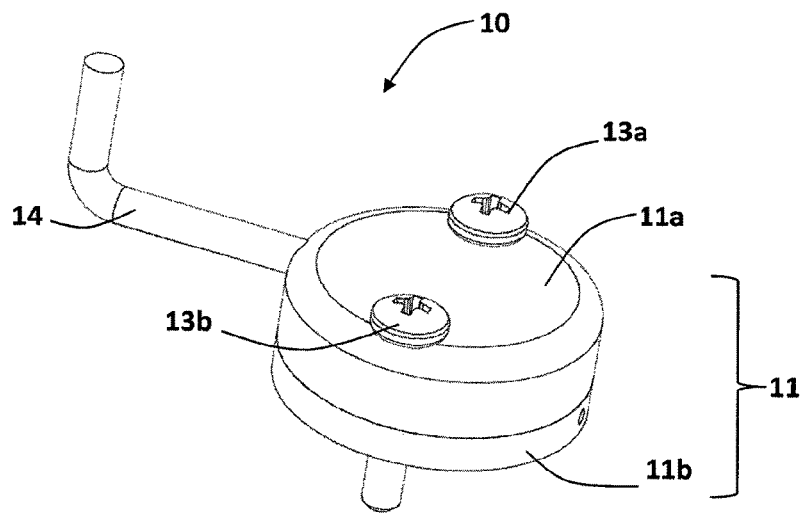
FIGS. 1A-1C show a measuring device for measuring fluid (water) potential in a plant tissue according to one embodiment of the invention.

In the following detailed description of various embodiments, reference is made to the accompanying drawings that form a part thereof, and in which are shown by way of illustration specific embodiments in which the invention may be practiced. It is understood that other embodiments may be utilized and structural changes may be made without departing from the scope of the present invention.

The present invention, in some embodiments thereof, provides a measuring device and a method for measuring fluid potential e.g. apoplastic water potential in plants via osmometry and a system including multiple such devices that can monitor and optionally also control irrigation status of one or more group of plants in which each plant or some of the plants have the device installed therein.

According to some embodiments, the measuring device is configured for being inserted into a part of the plant for measuring fluid potential thereof. The measuring device may be inserted into an incision cut through a part of the plant such as the plant's stem such that it engages the plant's inner tissue for measuring its fluid potential.

The measuring device may include (i) a body configured for being inserted into an incision in the plant, the body having a compartment walled by the body or part thereof configured for containing therein an osmoticum, where the compartment's body is ridged and includes one opening or a plurality of openings allowing thereby direct contact between the osmoticum and the plant fluid; (b) one or more selective barriers such as a membrane positioned at least over the opening(s) of the body for selectively allowing fluid transfer between the plant fluid and the osmoticum in the compartment; and (c) one or more pressure sensors each configured for detecting changes in pressure of fluid in the compartment.

The measuring device (also shortly referred to as "device") allows direct contact between the plant fluid and the osmoticum via the one or more selective barriers and measures the pressure caused by the natural fluid transfer (osmosis) inside the cavity occurring to chemically equilibrate the fluids' chemical potentials. Depending on the water potential in the plant's tissue water flows from one side of the selective barrier (e.g. The membrane) to the other. Since the selective osmoticum is encapsulated in a substantially ridged body bordering the compartment, the fluid flow translates into pressure changes inside the enclosed compartment. The measured pressure and changes thereof is directly correlated to the water potential of the plant which is a result of its irrigation status and possibly related to other environmental influences and thus enables direct and accurate measurement of the plant's water potential.

The measuring device is inserted into a freshly made incision or hole in the plant part such as the plant stem. The dimensions of the incision are such that the measuring device outer walls or some of them are in direct contact with the plant's tissue. The contact between the external wall of the measuring device's body and the plant's tissue allows fluids to flow via the selective barrier thereof to and from the osmoticum compartment. Salt and other organic materials dissolved in the water do not pass the fine selective barrier. The flow direction of the fluids is determined by the water potential in plant tissue, which depends on weather conditions, irrigation and other environmental effects. This water potential is matched to a constant water potential of concentrated solution (osmoticum) inside the device behind the selective barrier.

For example, after irrigation and during the night, as the plant tissue is saturated with water resulting in high water potential in the plant tissue. Such high potential results in water flow via the selective barrier into the osmoticum compartment. Since the volume of the osmoticum compartment is almost fixed due to the rigidity of the body bordering thereof, the added water causes the internal pressure to rise. Water osmotic flow is halted when the induced pressure equals the difference between the plant's water potential and the osmoticum chemical potential. During the day, as the plant losses water via it's leaves, the water potential inside the stem drops, resulting in water flow out of the osmoticum compartment. Such flow reduces the pressure inside the compartment.

The pressure changes inside the osmoticum compartment are measured by a pressure sensor positioned inside the cavity or externally thereto, where the measured pressure of the solution (osmoticum) therein is directly correlated to the water potential in the plant.

The water potential is therefore deduced from the output of the pressure sensor either using a processor that is embedded in the measuring device (such as by using a Micro Electro-Mechanical System (MEMS) having the sensor and the processor embedded therein) or by transmitting the sensor output to a remote location to be processed there.

According to some embodiments, the MEMS sensor includes a sensing unit and a microprocessor which controls the measurement and converts analog voltage outputted by the sensing unit into water potential correlated therewith. The water potential is then formatted into a digital signal indicative thereof, which can then be transmitted via said transmitter. In other embodiments the sensor does not include the processor but is external to the device connecting thereto via wires or other communication means. In this case the transmitter may also be external to the cover of the device embedded or connected to the processor. For example, in cases in which the device is designed to be inserted into a plant stem, the processor and transmitter are external to the stem.

According to some embodiments of the invention, the osmotic potential within the osmoticum compartment of the measuring device is set to be lower than the minimal potentials expected in the plant tissue to be measured.

The osmoticum may be any fluid such as a liquid solution or gel that allows osmosis based on potential gradient such as a water absorbent hydrogel e.g. Praestol 2500 polyamide or a liquid solution e.g. PolyEthyleneGlycol (PEG) or any other known in the art material. Different plant types may require different osmoticum or different osmoticum concentrations depending of their water potential range e.g. desired minimum of −1.2 MPa at fruit filling apple trees, or −2.0 MPa at grape vines before harvest.

Figure 1B:
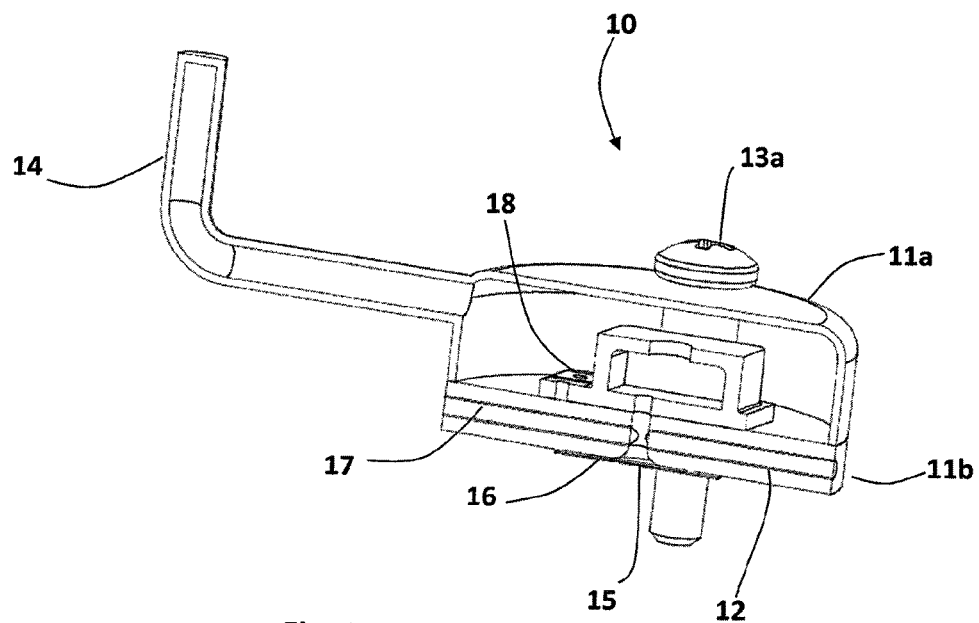
Figure 1C:
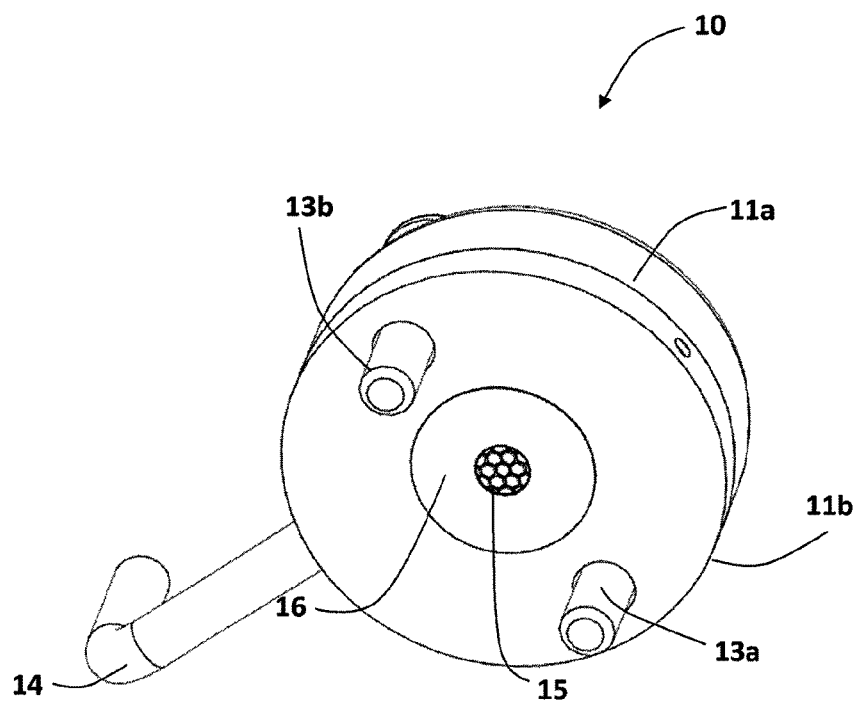

Reference is now made to FIGS. 1a-1c, which show an illustration of a measuring device 10 for measuring fluid (water) potential in a plant tissue according to some embodiments of the invention. According to those embodiments, the device 10 includes a housing 11 made of two housing elements 11a and 11b, connectable via connecting elements such as screws 13a and 13b. The lower housing element 11b has a compartment 12 therein in which osmoticum can be inserted. The compartment 12 has one upper opening over which a membrane selective barrier 15 is placed and held by a ridged support 16 (see FIGS. 1b and 1c). The device 10 further includes a MEMS sensor unit 18 connected to the lower housing element 11b. The MEMS sensor unit 18 is placed over an upper opening of the compartment 12 and seals this opening thereby. The compartment 12 is made by creating an elongated hole through the housing element 11b and sealing the compartment 12 surroundings by filling materials creating a filling layer 17 forming a cavity therein which is the compartment 12. The walls of the compartment 12 are substantially ridged forming a ridged compartment body.

The MEMS sensor unit 18 may include a pressure sensor and optionally a processor and optionally connects to wiring that can be inserted through a designated wiring tube 14 of the housing 11. Alternatively the processor connects to a transmitter for wirelessly communicating with the pressure sensor that is inside the plant to allow placing the processing unit outside the measuring device 10 housing 11 keeping the device 10 or part thereof that is designed for being inserted into the plant (e.g. The stem of the plant) as compact as possible.

The measuring device 10 or at least the housing 11 thereof is configured to be inserted into a small incision in the plant for allowing free and direct water flow between the osmoticum in the compartment 12 and the plant fluid.

According to some embodiments, the selective membrane 15 is designed to allow only sap water of the plant to enter the compartment preventing other non-water material from passing through its outer side facing the plant tissue into its inner side facing the compartment 12 and the osmoticum therein.

Other pressure sensors may be used for measuring changes in pressure in the compartment 12 for measuring (deducing) the water potential of the plant tissue being measured at each given timeframe. The pressure measuring may be done by the sensor continuously or frequently within predefined timeframes (such as every one or more seconds or minutes). The sensor data may be analyzed at a processor connected to the sensor of remotely by having the sensor unit include or connect to a transmitter. The analysis may include deducing the pressure changes over time of the plant water potential, deducing an irrigation status of the plant at each predefined timeframe and the like. This information may be presented over presentation means such as a screen connected or communicable with the measuring device for allowing users to irrigate the plant accordingly.

Figure 2A:
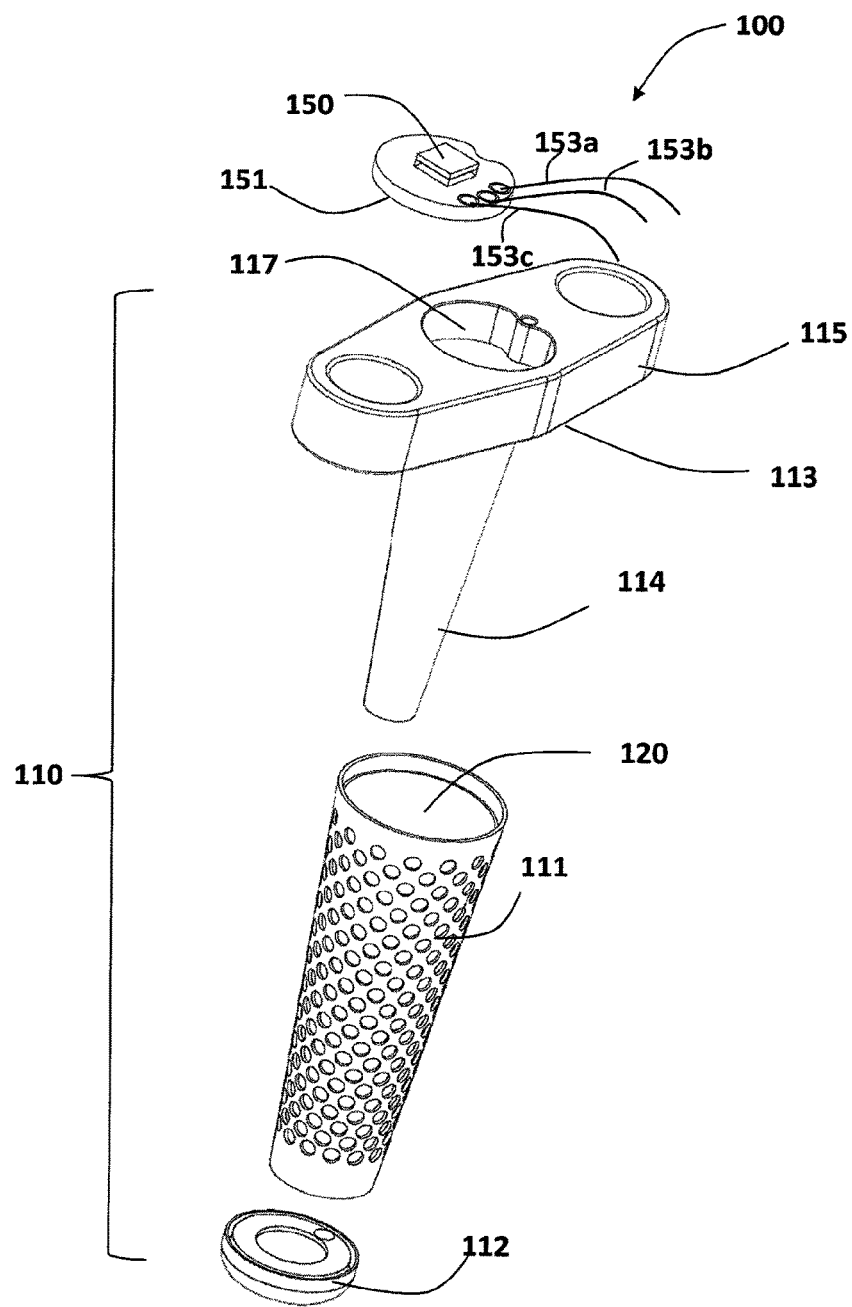
FIGS. 2A-2C show a measuring device for measuring fluid potential in a plant tissue having a conical body, according to another embodiment of the invention.
Figure 2B:
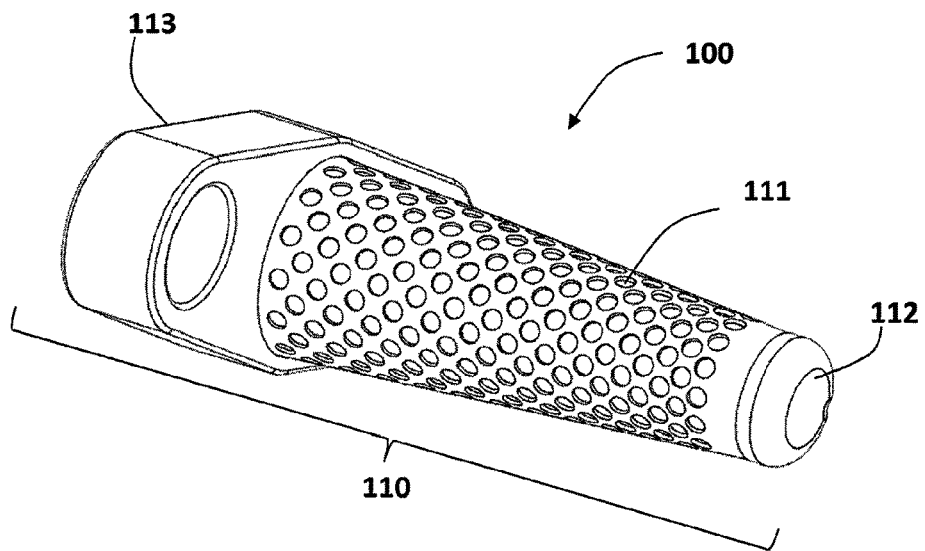
Figure 2C:
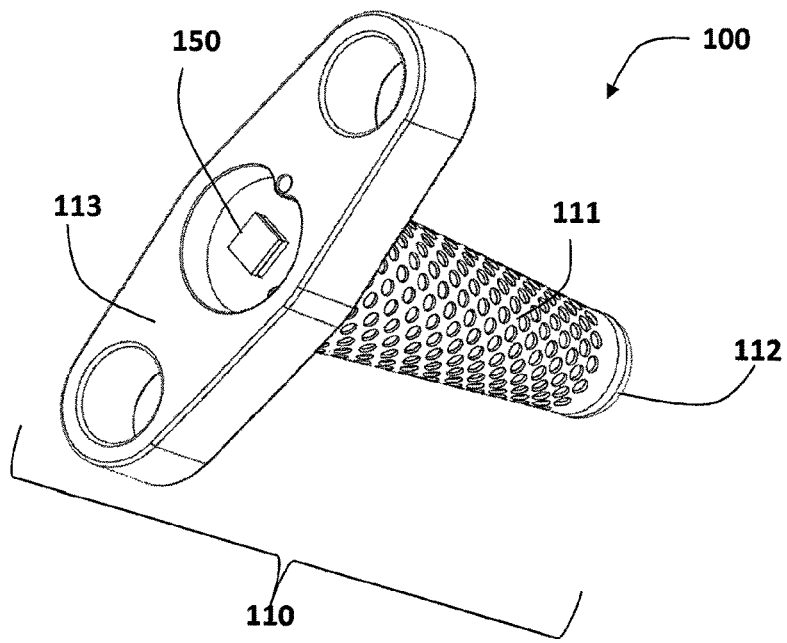

Reference is now made to FIGS. 2a-2c showing a measuring device 100 for measuring fluid potential in plant tissue, according to some embodiments of the invention. The device 100 includes: (i) a ridged body 110 constructed from three pieces: a porous enveloping member 111 having a conical shape, a first seal 112 for sealing one opening of the enveloping member 111 and a lid 113 configured for closing the other opening of the conical enveloping member 111, the body 110 forms a porous compartment configured for receiving an osmoticum therein; (ii) a selective barrier 120, which may be a reverse osmosis (RO) membrane, forwards osmosis (FO) membrane or nano filtration (NF) membrane or any other selective layer known in the art covering the walls of the enveloping member 111 from within; and (iv) a MEMS unit 150 including at least one pressure sensor, and optionally a processor and also a wireless transmitter embedded therein or connected externally thereto such as a radio frequency (RF) transmitter configured for wirelessly transmitting RF signals or an infrared (IR) optical transmitter configured for transmitting IR signals.

As shown in FIG. 2A and FIG. 2C, the lid 113 includes a cap 115 and an elongated member 114 configured for being inserted into a bore of the enveloping member 111 forming a space which is referred to herein as "cavity" of a compartment between the inner walls of the selective barrier 120 and the elongated member 114 inside the body 110 in which the osmoticum is inserted.

Once the device 100 is inserted into an incision in a plant such as a cut in a tree stem or other plant stem there is a direct contact between the osmoticum in the compartment of the body 110 and the plant fluid via the perforations in the porous enveloping member 111 and via the selective barrier 120.

The selective barrier 120 is designed to only allow passage of sap water into the compartment cavity preventing polluting materials from passing through. The passage of fluids through the selective barrier 120 and perforations of the enveloping member 111 occurs in accordance with the potential gradient between the plant fluid outside the compartment and the osmoticum in the compartment to equilibrate them. The changes in pressure inside the compartment of the body 110 is measured by a MEMS 150 sensor and the fluid potential at each given time frame is deduced from the sensor data. A tree surface mounted processor receives the sensor signal through wires 153a, 153b, and 153c and is configured for receiving the data from the sensor and processing it for calculating the fluid potential change of the plant or for transmitting the sensor data via its wireless transmitter to a remote unit that will process and analyze the sensor data for deducing various parameters associated with the plant water potential such as the plant water potential in each given timeframe and changes thereof over time, which are indicative of irrigation and/or other conditions of the plant.

It is shown in FIGS. 2A and 2C that the cap 115 includes a recess 117 for placing a platform 151 therein to which the MEMS sensor 150 is attached. In this particular example, the sensor is external to the cavity of the osmoticum but in other embodiments a probe of the sensor can be inserted into the cavity or the sensor (other than MEMS) or can be attached in the inner side of the walls of the cavity.

Figure 3:
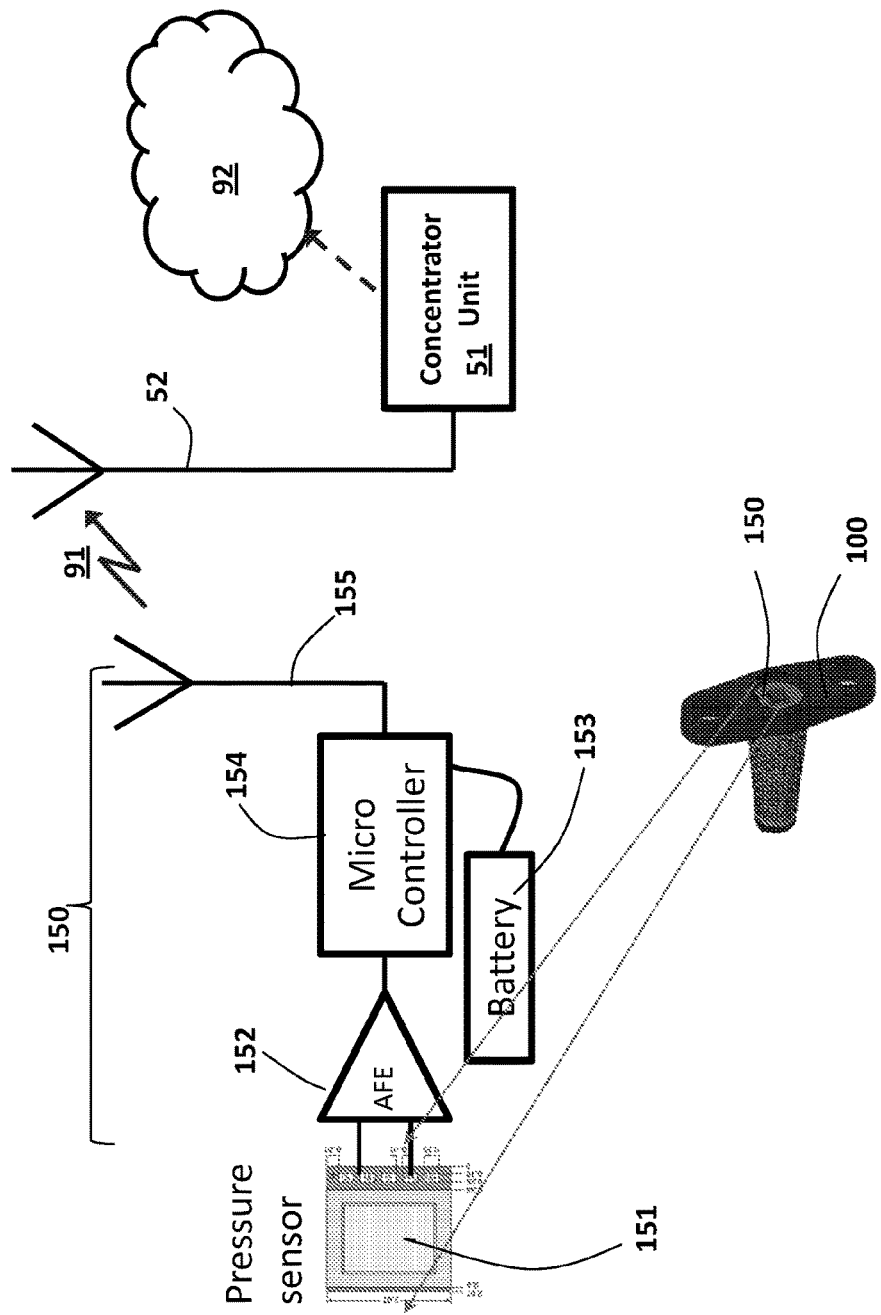
FIG. 3 shows a system for measuring fluid potential in plant tissue of group of plants via a remote data collection center configured for receiving sensors data, according to some embodiments of the invention.

FIG. 3 shows a system for measuring fluid potential in plant tissue of group of plants via a remote concentrator unit 51 configured for receiving data from pressure sensors of multiple measuring devices 100, according to some embodiments of the invention. The pressure sensor 151 connects via wires 153a, 153b and 153c to the microcontroller 154 on the tree MEMS sensor 150 via an analog front end (AFE) 152 which electronic components responsible for extraction and conditioning of analog signals into digital data, powered by a battery 153, where the microcontroller 154 connects to a wireless transmitter 155 for transmitting the sensor data or data deduced therefrom such as the fluid potential in each given moment or timeframe to the remote concentrator unit 51 via wireless communication network such as, for instance through a radio frequency (RF) based communication link 91 The concentrator unit 51 receives sensor data through link 91 from a group of trees equipped with transmitting sensors, and re-transmit the data via wired or wireless means e.g. GPRS modems, to the Internet.

Figure 4:
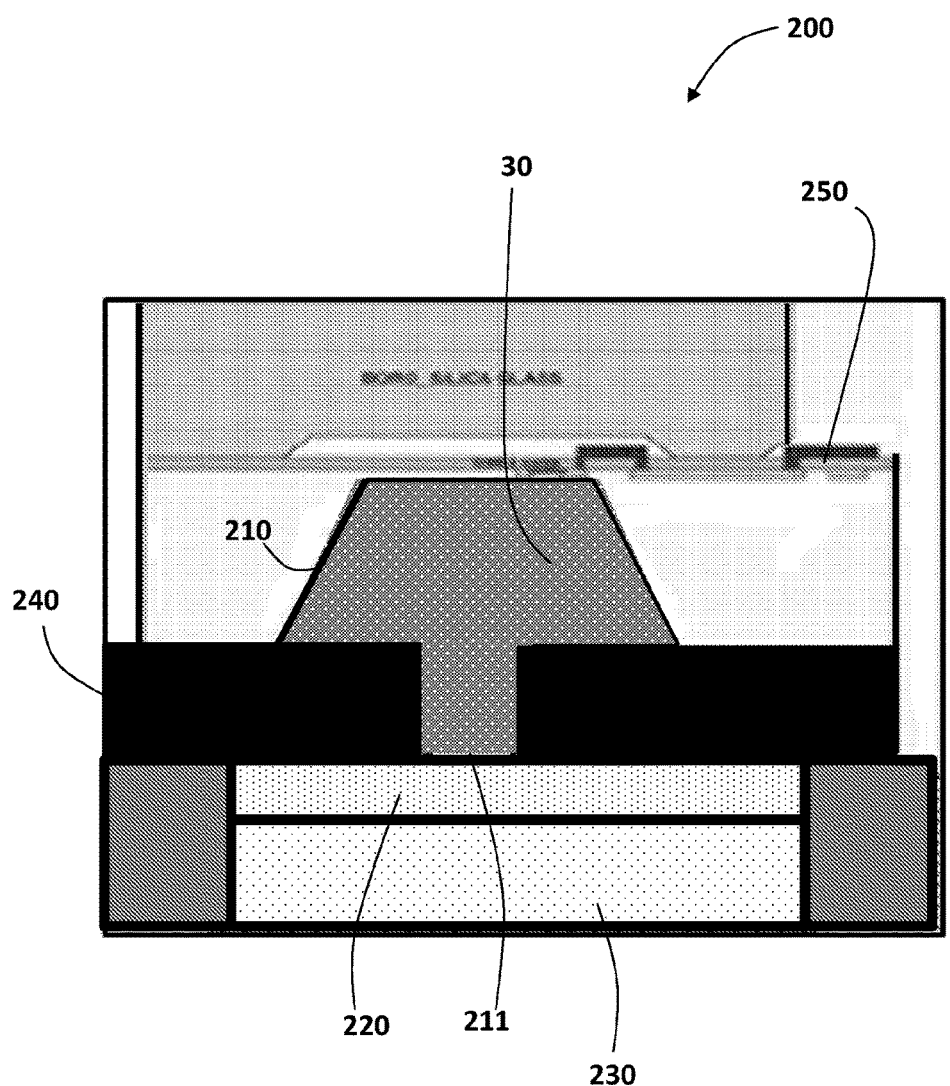
FIG. 4 shows a measuring device for measuring fluid potential in a plant tissue having a flattened body, according to another embodiment of the invention.

FIG. 4 shows a measuring device 200 for measuring fluid potential in a plant tissue having a flattened body, according to another embodiment of the invention. The measuring device 200 in this case has a flattened rectangular shape having a compartment 210 forming a cavity therein, in which the osmoticum 30 is inserted. The body 210 has one opening 211 defined by a barrier 240 where two layers cover the opening 211 externally thereto: the first is a selective membrane 220 barrier placed over the opening and the second is a rigid porous pad 230 layered over the membrane 220. The fluid of the plant is in continuum contact with the osmoticum in the compartment 210 via the barriers 220 and 230 ensuring that only sap water of the plant fluid can enter the compartment 210.

According to some embodiments, An absolute pressure sensor 250 located above the compartment 210 senses the pressure therein caused by fluids flowing into or out of the compartment 210 via its opening 211 in response to the fluid potential gradient between the plant fluid and the osmoticum.

Figure 5:
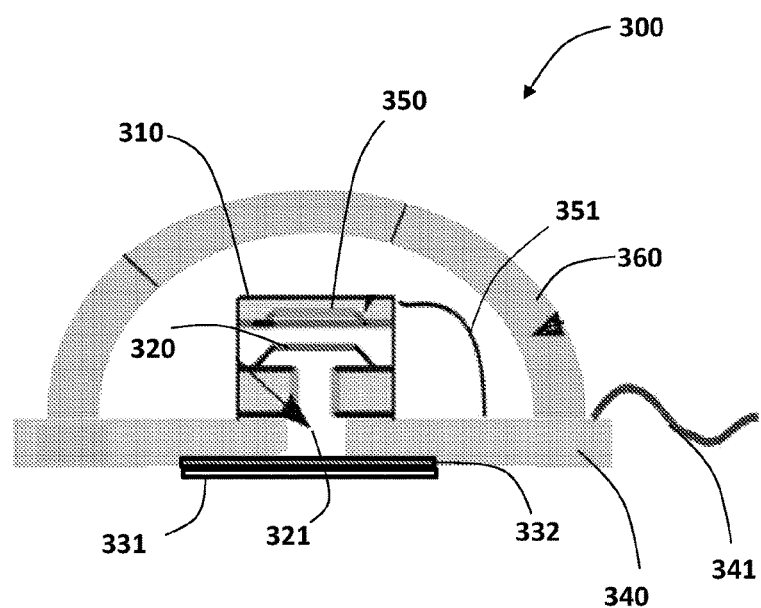
FIG. 5 shows a measuring device for measuring fluid potential in a plant tissue having a flattened body covered by a semi-spherical cover, according to another embodiment of the invention.

FIG. 5 shows a measuring device 300 for measuring fluid potential in a plant tissue having a flattened body 310 protected by a semi-spherical cover 360, according to another embodiment of the invention. The device 300 body 310 encloses a compartment 320 therein having ridged walls forming therein a cavity in which the osmoticum is located. The compartment 320 has one opening 321 and is externally covered by two selective barriers: a membrane 331 and a porous pad 332 for allowing continuum contact between the fluid of the plant and the osmoticum via the barriers 331 and 332. A MEMS pressure sensor 350 is positioned over the compartment 320 for measuring pressure therein and connects to a printed circuit board (PCB) 340 via an electric connector 351. The overall shape of the measuring device 300 will be a semi-sphere configured for being inserted into a corresponding semispherical opening cut in the plant stem of other part of the plant.

All types of measuring devices such as devices 100, 200 and 300 may be configured for measuring plant fluid from the plant's vascular conduits such as the plant stem xylem and/or from other parts of the plant. The same design of measuring device may be able to measure fluid potential in various types of plants and in various types of plant types or parts. This requires that the initial pressure inside the compartment having the osmoticum therein will fit the specific plant type that is to be measured depending on its average known lowest and/or highest potential in over-irrigation and under-irrigation conditions for example. This known pressures range or threshold depends on various factors of the device itself such as the rigidity and size of the walls of the compartment, the selective barrier(s) holes density, the specific osmoticum consistency and type and the like.

In one example, the measuring device is configured for measuring water potential in xylem of a tree stem, and therefore incision is made in the tree stem reaching very close to the xylem (without injuring thereof) to have the device placed therein.

Figure 6:
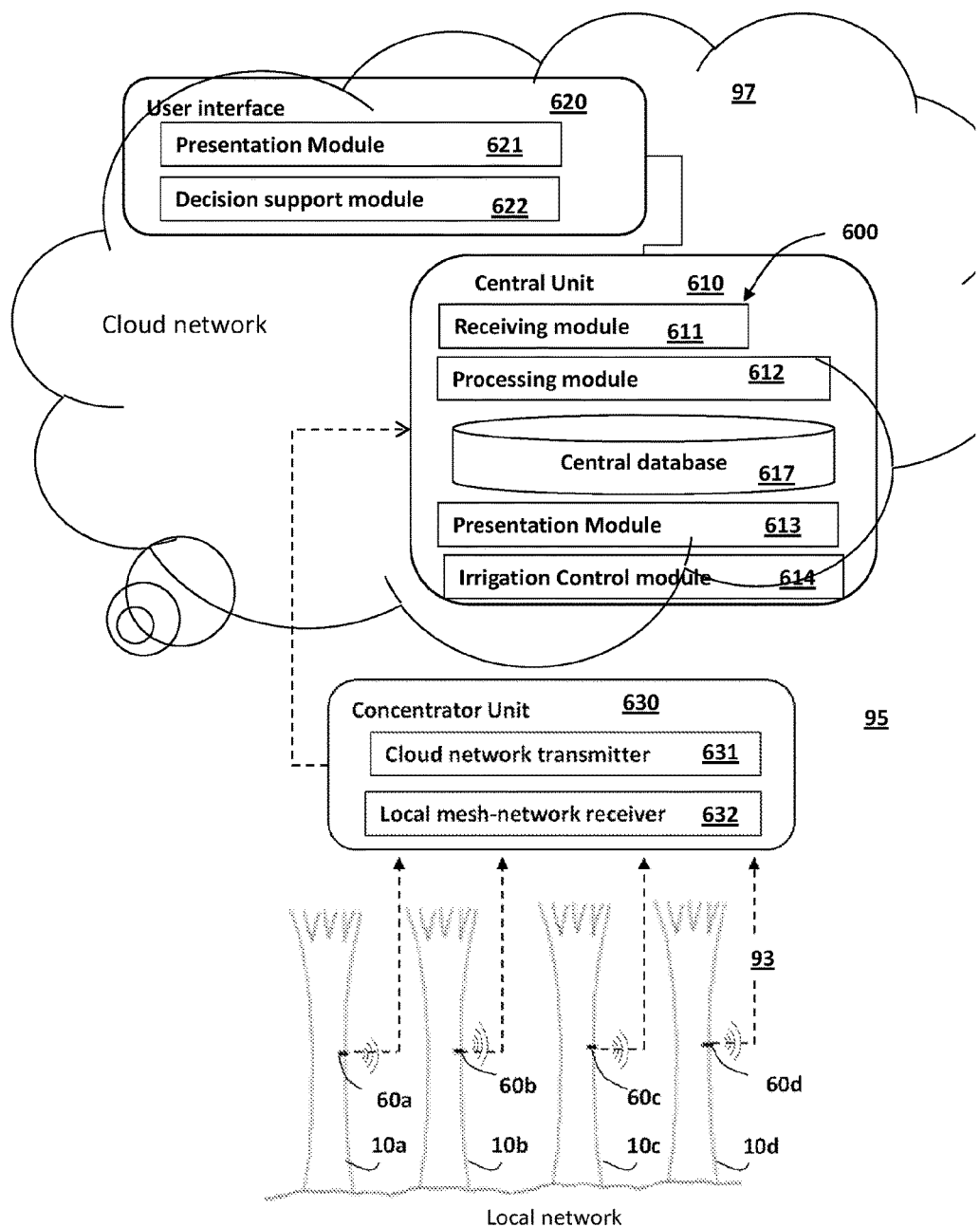
FIG. 6 shows a system for measuring fluid potential in plant tissue of a group of plants via a remote data collection center configured for receiving sensors data from multiple measuring devices, according to some embodiments of the invention.

FIG. 6 shows a system 600 for monitoring and measuring fluid potential in vascular conduits of a group of plants such as trees 10a-10d via a remote central unit 610 configured for receiving sensors data via a concentrator unit 630, from multiple measuring devices such as measuring devices 60a-60d, each inserted into incisions in one of the tree stems of trees 10a-10b, according to some embodiments of the invention.

Each measuring device 60a-60d of each tree 10a-10d is configured to transmit data from its sensor or processed data thereof via one or more wireless communication links such as through a RF link 93 to the central unit 610, where this data is accumulated and processed.

According to some embodiments, the concentrator unit 630 is configured for concentrating information received via data transmission from all the measuring devices 60a-60d and transmitting this data and optionally additional data associated therewith to the remotely stationed central unit 610 via a concentrator 630 via a cloud network 97. The concentrator unit 630 includes a cloud network transmitter

631 and a local mesh network receiver 632 to receive the measuring devices' data using a shorter range local network 95 such as a wireless communication link e.g. wi-fi, zig-bee and the like.

According to some embodiments, as illustrated in FIG. 5, the central unit 610 includes one or more receiving modules such as receiving module 611 for receiving the data from the concentrator unit's transmitters 631 which may either be their pressure sensors data or data related thereto such as the measured water potential in respect to the specific timeframe (calculated from the sensor data); and a processing module 612 for processing and analyzing the received sensor/sensor related data for example for identifying the changes in the water potential of each tree 10a-10d over time and/or for identifying an overall condition of the trees 10a-10d to allow controlling irrigation and possibly other effecting processes such as determining amounts and types of fertilizers to be added and scheduling of fertilization and irrigation and the like.

The system 600 allows optimizing irrigation and other processes for yielding the best crops at the exact required amounts of water and other substances required for healthy and optimal growth and yield from those plants that the system 600 monitors.

The system 600 may include software and hardware modules enabling to process data and optionally may also include one or more presentation means controlled by a presentation module 613 for presenting the information of the analysis results and/or the received data.

The system 600 may be designed to be set to monitor various kinds of measuring devices in various types of plants so that it can be adapted to monitor different plant groups (different crops and fields thereof).

According to some embodiments, to identify irrigation condition of the plants in the group, the system 600 processing module 612 operable via one or more computer processors, may be programmed to compare the pressure of the sensor to a predefined lower threshold pressure corresponding to a low-irrigation condition and to an upper pressure threshold corresponding to an over-irrigation condition of the particular plant type that is being monitored. To adapt the system 600 to a group of different plant type, an administrator may be required to changes the values of the lower and upper thresholds, for example the 0.8 to 1.2 MPa (negative) stem water potentials optimum range in apple trees.

According to some embodiments, as shown in FIG. 6 the central unit 610 may also include an irrigation control module 614 configured for operating and controlling an irrigation means 620 that may be part of the system 600 or separated therefrom. The irrigation module 614 is also configured for determining an irrigation plan and time span thereof for irrigating the plants 10a-10b of the control group according to their measured fluid potential over time by, for example, determining irrigation amounts and schedules. The irrigation module may also provide plans for other related processes such as for fertilization schedules and amounts, fertilizers types, determine whether the crops should be protected by covers, disinfested, replanted and the like. In other embodiments, the irrigation module 614 simply presents these plans and does not necessarily control the actual automated irrigation means.

The central unit 610 may further include or have access to one or more databases such as central database 617 for storing the received and analyzed data and other information associated therewith such as the date, the time of the day associated with each measurement and the like.

According to some embodiments, as illustrated in FIG. 6, the central unit 610 may be configured to allow access to one or more remote user devices such as user device having a designated application operated thereby for viewing the data such as the measured potentials and/or the irrigation status and/or irrigation plans associated therewith via a special presentation module 621 in the application interface 620. The application optionally also provides a decision support module 622 for allowing a user to remotely control irrigation. The application may also enabling browsing through the database 617 of the central unit 610 for data retrieval.

Figure 7:
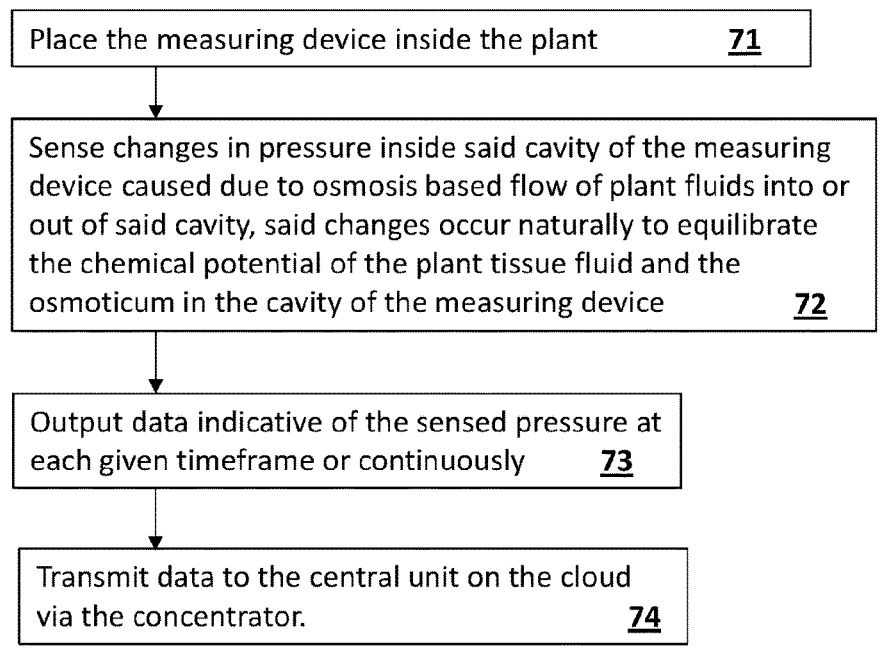
FIG. 7 is a flowchart of a process for measuring fluid potential in plant tissue using a measuring device, according to some embodiments of the invention.

FIG. 7 is a flowchart of a process for measuring fluid potential in plant tissue using a measuring device having a ridged compartment with an osmoticum therein having at least one opening, at least two selective barrier layers covering the one or more openings of the compartment, and a pressure sensor, according to some embodiments of the invention.

The process includes making an incision inside the plant at a desired location thereover such as in the plant stem and inserting the measuring device therein 71; sensing pressure inside the osmoticum compartment using the device's pressure sensor 72, wherein the sensor data is outputted 73 continuously or discretely at each given timeframe. The sensor data can be received by a concentrator unit serving as a relay station having a receiver and a transmitter and then sent by the concentrator unit to a remote unit for further processing of the sensor data 74 via a cloud network based communication link.

Figure 8:
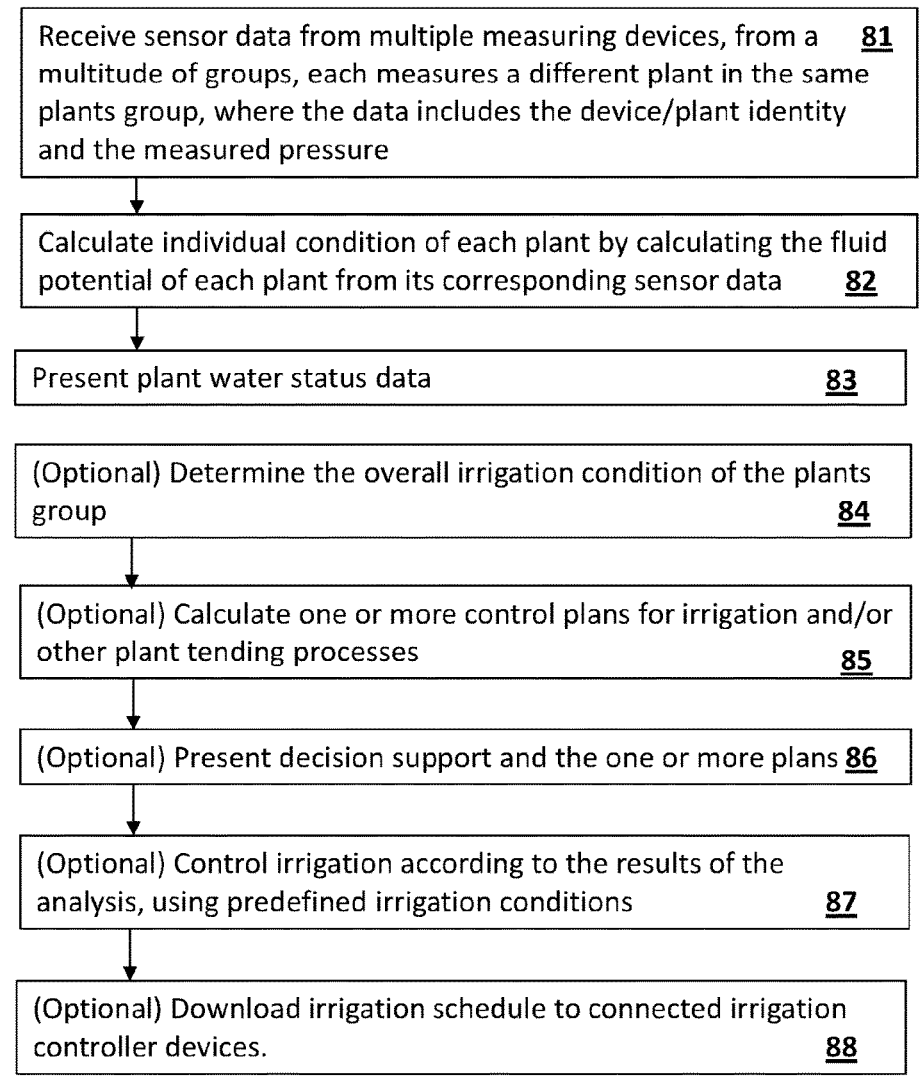
FIG. 8 is a flowchart of a process for analyzing condition of multiple plants using a unified central processing center receiving data from multiple measuring devices, according to some embodiments of the invention.

FIG. 8 is a flowchart of a process for analyzing condition of multiple plants using a unified central processing center receiving data from multiple measuring devices, according to some embodiments of the invention. This process first includes receiving sensor data from multiple measuring devices, each installed at a different plant of the same plant group to be monitored 81, wherein the data may be indicative of the identity of the specific plant and the sensed pressure or another parameter associated therewith. The data may be transmitted via a wireless communication link such as via RF communication via a transmitter embedded in the measuring device or connected thereto.

The received data is then processed to calculate individual condition of each of the plants such as its irrigation status or condition deduced from the pressure or associated and calculated fluid potential of each plant 82 the calculated irrigation status is then presented 83. Optionally, the overall irrigation condition of all the plants in the group that is monitored may be calculated 84 for determining the causes of the plants condition. One or more control plans are then calculated and designed automatically through the system computer means for example for irrigating all the plants in the group or for each plant individually 85. This plan is then presented 85 via presentation means of the system to allow an authorized person to view and control the irrigation or other factor effecting the plants' growth accordingly. Additionally or alternatively the control may be done automatically through automated irrigation means for instance 87. Optionally an irrigation plan including irrigation schedules can be downloaded to the controller for controlling irrigation of the plants group according to the scheduling in the irrigation plan.

Figure 9A:
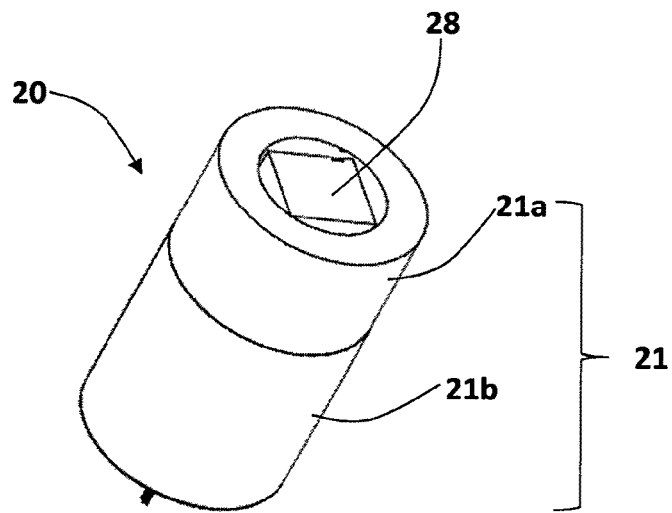
FIGS. 9A-9C show a measuring device for measuring fluid (water) potential in a plant tissue according to another embodiment of the invention.
Figure 9B:
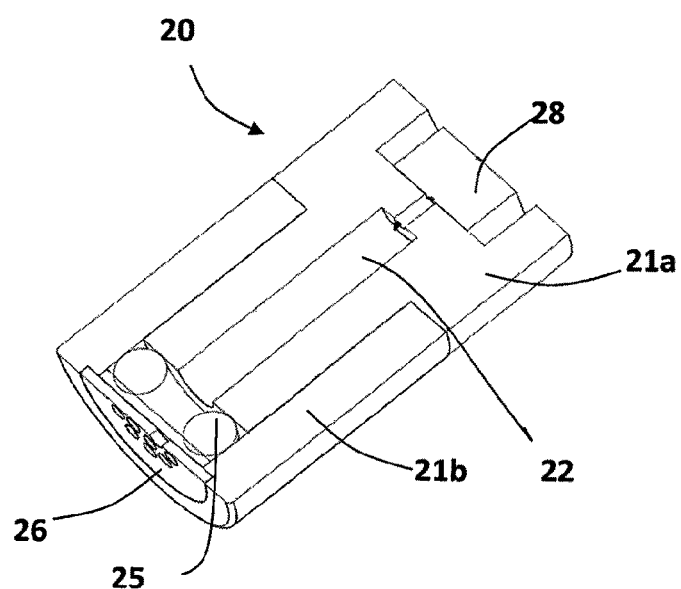
Figure 9C:
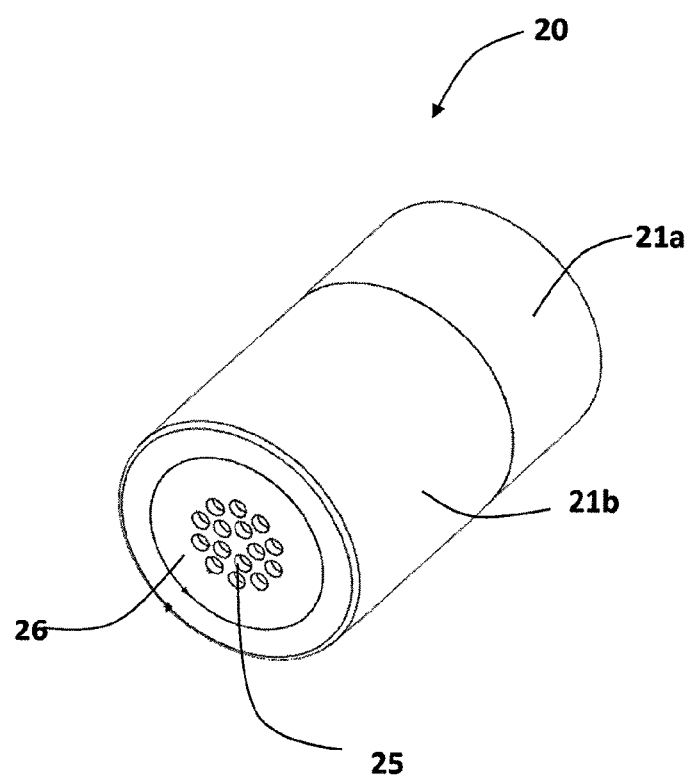

Reference is now made to FIGS. 9a-9c, which show an illustration of a measuring device 120 for measuring fluid (water) potential in a plant tissue according to other embodiments of the invention. According to those embodiments, the device 20 includes a housing 21 made of two housing elements 21a and 21b, connectable via connecting elements such as screws or snap connection. The lower housing element 21b has a compartment 22 therein in which osmoticum can be inserted. The compartment 22 has one upper opening over which a membrane selective barrier 25 is placed and held by a porous ridged support 26 (see FIGS. 9b and 9c). The device 20 further includes a MEMS sensor unit 28 connected to the lower housing element 21b. The MEMS sensor unit 28 is placed over an upper opening of the compartment 22 and seals this opening thereby. The compartment 22 is made by creating an elongated hole through the housing element 21b and sealing the compartment 22. The walls of the compartment 22 are substantially ridged forming a ridged compartment body.

The MEMS sensor unit 28 may include a pressure sensor and optionally a processor and is optionally connect to wiring that can be inserted through a designated wiring tube of the housing 21. Alternatively the processor connects to a transmitter for wirelessly communicating with the pressure sensor that is inside the plant to allow placing the processing unit outside the measuring device 20 housing 21 keeping the device 20 or part thereof that is designed for being inserted into the plant (e.g. The stem of the plant) as compact as possible.

The measuring device 20 or at least the housing 21 thereof is configured to be inserted into a small incision in the plant for allowing free and direct water flow between the osmoticum in the compartment 22 and the plant fluid.

According to some embodiments, the selective membrane 25 is designed to allow only sap water of the plant to enter the compartment preventing other non-water material from passing through its outer side facing the plant tissue into its inner side facing the compartment 22 and the osmoticum therein.

Other configurations of the measuring device may be implemented combining, for example, various components of the devices shown above. For example the gauge sensor may be implemented in the conically shaped measuring device instead of the MEMS sensor and the like. Various types of sensors may be used for the various configuration of the compartments of the devices and various configurations, types and locations of the selective one or more barriers.

According to other embodiments of the invention, the measuring device simply includes one or more selective barriers entirely encapsulating the osmoticum therein such as a porous ridged body and/or a ridged membrane having no completely sealed section of the compartment. In fact the compartment body is the selective barrier itself forming a cavity therein for containing the osmoticum. The sensor is located inside or over the selective barrier compartment for sensing pressure changes therein.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments and/or by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Although the invention has been described in detail, nevertheless changes and modifications, which do not depart from the teachings of the present invention, will be evident to those skilled in the art. Such changes and modifications are deemed to come within the purview of the present invention and the appended claims.

What is claimed is:

1. A method for measuring fluid potential in a plant tissue, said method comprising the steps of:
   a) placing at least part of a device for measuring fluid potential in a plant tissue inside the plant such that said at least part of said measuring device creates hydraulic continuum with the plant tissue, wherein the device comprises:
      i. a compartment having a ridged body configured for containing therein an osmoticum which is a water absorbent hydrogel, said compartment comprising at least one opening;
      ii. at least two selective barrier layers positioned at least over said at least one opening of said compartment for selectively allowing water transfer between the plant fluid and the osmoticum in the compartment, wherein said compartment is configured such that there is a direct contact between the plant fluid and the osmoticum within said compartment via said at least two selective barrier layers; and iii. at least one pressure sensor configured for detecting changes in pressure of fluid in said compartment, said changes being related to the water potential of the plant tissue;

wherein said at least two selective barrier layers are configured to selectively allow transfer of water therethrough, while blocking transfer of other ingredients in the plant fluid, b) sensing changes in pressure caused due to osmosis based flow of fluids into or out of said compartment caused to equilibrate the chemical potential of the plant tissue fluid and the osmoticum in the compartment; and c) outputting data indicative of the sensed pressure changes, said changes being related to the fluid potential of the plant tissue.

2. The method according to claim 1, wherein one selective barrier layer of said at least two selective barrier layers is a membrane selected from the group consisting of a reverse osmosis (RO) membrane, forward osmosis (FO) membrane or a Nano filtration (NF) membrane.

3. The method according to claim 1, wherein said osmoticum comprises PolyEthyleneGlycol (PEG).

4. The method according to claim 1, wherein said at least one pressure sensor is selected from the group consisting of: at least one piezoelectric transducer sensor; at least one strain gauge sensor or a combination thereof.

5. The method according to claim 1, wherein the device further comprises a microprocessor and a transmitter connected to said at least one pressure sensor for reading, digitizing, and transmitting sensor data thereby.

6. The method according to claim 5, wherein the device further comprises at least one Micro Electro-Mechanical System (MEMS) comprising said pressure sensor, said data microprocessor and said transmitter within said MEMS.

7. The method according to claim 5, wherein said transmitter is configured for wirelessly transmitting one of: RF (radio frequency) signals or IR (Infrared) signals.

8. The method according to claim 5, wherein said pressure sensor comprises a sensing unit and a microprocessor which controls said measuring fluid potential and converts analog voltage outputted by the sensing unit into water potential correlated with said analog voltage and converts said water potential into a digital signal indicative of said water potential, which can then be transmitted via said transmitter.

9. The method according to claim 1, wherein said compartment is configured for being hydraulically connected to a vascular conduit of the plant, via the free space ("apoplast") of the plant tissue, wherein said fluid potential that is measured is plant sap water conducted through said vascular conduit.

10. The method according to claim 1, wherein said compartment forms a flattened shape forming a cavity for containing the osmoticum therein and a single opening, wherein said at least two selective barrier layers are located over said opening of said compartment at an internal or external side thereof, wherein the fluid potential within the cavity is initially set to be lower than the minimal potentials expected in the plant tissue to be measured.

11. The method according to claim 1 further comprising the steps of:

a) receiving outputted data from said at least one pressure sensor; and b) calculating the fluid potential in said plant according to the sensed pressure at each given timeframe.

12. The method according to claim 11 further comprising transmitting data outputted by said at least one pressure sensor to a processing unit, configured for conducting calculation of the fluid potential associated with the sensor output data.

13. The method according to claim 1, wherein said measuring device is placed in proximity to at least one vascular conduit of the plant or is inserted to the apoplast of the stem of the plant.

* * * * *